United States Patent
Ishibashi et al.

(10) Patent No.: US 6,692,768 B1
(45) Date of Patent: Feb. 17, 2004

(54) PREPARATION METHOD OF DRUG-CONTAINING SPHERICAL FINE PARTICLES

(75) Inventors: Takashi Ishibashi, Sakai (JP); Keigo Nagao, Kawanishi (JP); Kengo Ikegami, Nishinomiya (JP); Hiroyuki Yoshino, Suita (JP); Masakazu Mizobe, Takatsuki (JP)

(73) Assignee: Tanabe Seiyaku Co., Ltd., Osaka (JP)

( * ) Notice: Subject to any disclaimer, the term of this patent is extended or adjusted under 35 U.S.C. 154(b) by 0 days.

(21) Appl. No.: 09/830,345

(22) PCT Filed: Oct. 22, 1999

(86) PCT No.: PCT/JP99/05833

§ 371 (c)(1),
(2), (4) Date: Apr. 26, 2001

(87) PCT Pub. No.: WO00/24379

PCT Pub. Date: May 4, 2000

(30) Foreign Application Priority Data

Oct. 26, 1998 (JP) ............................................. 10-303784

(51) Int. Cl.$^7$ ............................ A61K 9/16; A61K 9/14; A61K 9/10; A61K 9/20; A61J 3/06
(52) U.S. Cl. ....................... 424/489; 424/468; 424/469; 424/470; 424/474; 424/482; 424/501; 424/499
(58) Field of Search ................................ 424/501, 499, 424/489, 482, 468, 469, 470, 474

(56) References Cited

U.S. PATENT DOCUMENTS

| | | | |
|---|---|---|---|
| 3,084,104 A | * | 4/1963 | Tuerck et al. ................. 167/82 |
| 5,547,683 A | * | 8/1996 | Yano et al. ................... 424/501 |
| 5,674,533 A | | 10/1997 | Santus et al. |
| 6,063,313 A | * | 5/2000 | Briskin et al. ................ 264/15 |

FOREIGN PATENT DOCUMENTS

| | | |
|---|---|---|
| EP | 0 359 195 A2 | 3/1990 |
| EP | 0 407 325 A1 | 1/1991 |
| EP | 0 608 850 A1 | 8/1994 |
| EP | 0616841 A1 | 9/1994 |
| EP | 000616841 A1 * | 9/1994 |
| EP | A1616841 | 9/1994 |
| JP | A05229961 | 9/1993 |
| JP | A06056700 | 3/1994 |
| JP | A6056700 | 3/1994 |
| WO | WO 97/10810 A2 | 3/1997 |

OTHER PUBLICATIONS

Abstract of the 5th Symposium for Pharmaceutical Preparations and Particle Design, pp. 68–73 (1988) (with English Translation).

Shah, Ketan P., et al., International Journal of Pharmaceuticals, vol. 109, pp. 271–281, 1994.

Seminer, Eudragit et al., pp. 39–54, 1997 (with partial English translation).

* cited by examiner

Primary Examiner—Thurman K. Page
Assistant Examiner—Rachel M. Bennett
(74) Attorney, Agent, or Firm—Birch, Stewart, Kolasch & Birch, LLP

(57) ABSTRACT

The present invention discloses an efficient preparation method of spherical fine particles containing a drug for an easily-swallowed, controlled-release preparation comprising the production of drug-containing spherical fine particles (mean particle size: 60–200 $\mu$m) by adding a binder solution to a mixture containing an excipient powder having the property of retaining solvent (and preferably having a mean length of the long axis of 40 $\mu$m or less) and a drug powder (preferably having a mean length of the long axis of 50 $\mu$m or less), followed by high-speed mixing granulation.

16 Claims, 1 Drawing Sheet

PREPARATION METHOD OF DRUG-CONTAINING SPHERICAL FINE PARTICLES

This application is the national phase under 35 U.S.C. §371 of PCT International Application No. PCT/JP99/05833 which has an International filing date of Oct. 22, 1999, which designated the United States of America.

TECHNICAL FIELD

The present invention relates to a preparation method of drug-containing spherical fine particles that are useful in the production of easily-swallowed, controlled-release preparations.

BACKGROUND ART

Research has been conducted on various types of controlled-release preparations in order to reduce the number of medication times and alleviate adverse side-effects in the case of oral administration of a medication to a patient, and such preparations are widely used clinically as well.

However, since controlled-release preparations of the prior art are used primarily in the form of tablets, granules, capsules and so forth, they have problems in terms of being accompanied by difficulties in swallowing the medication for infants, elderly persons, seriously ill patients and so forth having decreased swallowing abilities. Thus, there is a need for more improved, easily-swallowed, controlled-release preparations.

In order to solve the above problems, orally rapid-disintegrating tablets and suspensions, etc. that contain controlled-release fine particles have been proposed. However, it is preferable that the particle size of these preparations be 200 µm or less to avoid an unpleasant sensation in the oral cavity when taken (see International Journal of Pharmaceutics 109, 271–281 (1994)), or it is necessary to improve the content of pharmaceutical in controlled-release fine particles in order to reduce the amount taken.

Consequently, when producing an easily-swallowed, controlled-release preparation, a method is required for efficiently producing particles having a high pharmaceutical content at the core of the particles, small particle size, narrow particle size distribution width, high sphericity and a smooth surface that is easily coated.

As an example of a granulation technology of the prior art, although a method for producing coating cores for fine granules by granulation is described in Japanese Unexamined Patent Publication No. 6-56700, the content of pharmaceutical in the coating cores is 5% or less, and the mean particle size is 270µ or more.

In addition, Japanese Unexamined Patent Publication No. 5-229961 describes in Example 2 that particles produced by centrifugal fluidizing granulation after adding water to lactose and cellulose crystals are spherical, and that 80% of the particles have a particle size within the range of 150–250 µm. However, this relates to a method for producing particles used as an excipient that does not contain a pharmaceutical.

In general, the efficient production of particles of 200 µm or less by agitating granulation has been considered to be difficult (see 7th Eudragit Seminar, 1997, pp. 39–54).

DISCLOSURE OF THE INVENTION

The present invention provides a method for efficiently producing particles having a high drug content, small particle size, high sphericity, smooth surface and an easily coated form required for the production of easily-swallowed, controlled-release preparations.

As a result of conducting various studies, the inventors of the present invention discovered that drug-containing spherical fine particles for easily-swallowed, controlled-release preparations can be efficiently produced by a simple means comprising adding a binder solution to a mixture containing a drug powder and an excipient powder having the property of retaining solvent, followed by high-speed mixing granulation, thereby leading to completion of the present invention.

Namely, the present invention relates to a preparation method of drug-containing spherical fine particles having a mean particle size of 200 µm or less comprising: adding a binder solution to a mixture containing an excipient powder having the property of retaining a solvent and said drug powder, and granulating by high-speed mixing.

To begin with, the following provides an explanation of the materials used in the method of the present invention.

[1] The excipient used in the method of the present invention having the property of retaining solvent (to be abbreviated as the solvent-retaining excipient) is an excipient that has the property of non-bonding absorption of solvent and can be formed into fine particles. This excipient is suitably selected according to the type of drug, solvent and so forth. The excipient is preferably that in which the solvent retention rate is 2–50% of its dry weight, and particularly preferably 5–30%.

Furthermore, the solvent retention rate here refers to the proportion of the maximum amount of solvent retained internally by the excipient at room temperature and under normal pressure to the weight of the excipient in the form of having retained solvent (including the solvent weight), expressed as a percentage. This can be calculated by measuring the weight during maximum retention of solvent in the excipient and the weight when the solvent has been completely removed.

A water-retentive excipient is preferably used as the solvent-retaining excipient, specific examples of which include celluloses such as microcrystalline cellulose, methyl cellulose, sodium carmelose, calcium carmelose and low-substituted hydroxypropyl cellulose, and starches such as wheat starch, rice starch, corn starch, potato starch, hydroxypropyl starch, sodium carboxymethyl starch, α-cyclodextrin and β-cyclodextrin. The most preferable examples of solvent-retaining excipients are microcrystalline cellulose and corn starch.

The solvent-retaining excipient is used in the form of a powder, has a mean length of the long axis of 40 µm or less, and preferably 1–30 µm, and that smaller than the mean length of the long axis of the drug particles mentioned below is preferable.

Although the amount of solvent-retaining excipient used varies according to the solubility of the drug in the solvent, the type of solvent, amount of solvent and so forth, it is normally 3–50 wt % of the drug, and preferably 5–30 wt % of the drug.

[2] The drug used in the method of the present invention dissolves in the solvent and can be formed into fine particles. A drug having solubility in the solvent at 25° C. of 1 g in 1 liter of solvent, and preferably 10 g or more in 1 liter of solvent, is used.

Specific examples of drugs are listed below.

(1) Antipyretics, analgesics and antiphlogistics such as indometacin, aspirin, diclofenac sodium, ketoprofen, ibuprofen, mefenamic acid, azulene, phenacetin, isopropyl antipyrine, acetaminophen, benzadac, phenylbutazone, flufenamic acid, sodium salicylate, salicylamide, sazapyrine and etodolac; (2) steroid anti-inflammatory drugs such as dexamethasone, hydrocortizone, prednisolone and triamcinolone; (3) antiulcer drugs such as ecabet sodium, enprostil, sulpiride, cetraxate hydrochloride, gefarnate, irsogladine maleate, cimetidine, ranitidine hydrochloride, famotidine, nizatidine and roxatidine acetate hydrochloride; (4) coronary vasodilators such as nifedipine, isosorbide dinitrate, diltiazem hydrochloride, trapidil, dipyridamole, dilazep hydrochloride, verapamil, nicardipine hydrochloride and verapalimil hydrochloride;

(5) peripheral vasodilators such as ifenprodil tartrate, cinepacide maleate, ciclandelate, cynnaridine and pentoxyphylin; (6) antibiotics such as ampicillin, amoxicillin, cefalexin, erythromycin ethyl succinate, vacampicillin hydrochloride, minocycline hydrochloride, chloramphenicol, tetracycline, erythromycin, ceftazidime, cefuroxime sodium, aspoxicillin and lichipenam acoxyl hydrate; (7) synthetic antimicrobials such as nalidixic acid, piromidic acid, pipemidic acid trihydrate, enoxacin, cinoxacin, ofloxacin, norfloxacin, ciprofloxacin hydrochloride and sulfamethoxazole-trimethoprim; (8) antiviral agents such as aciclovir and ganciclovir; (9) anticonvulsants such as propantheline bromide, atropine sulfate, oxitropium bromide, timepidium bromide, scopolamine butylbromide, trospium chloride, butropium bromide, N-methylscopolamine methylsulfate and methyloctatropine bromide;

(10) antitussives such as tipepidine hibenzate, methylephedrine hydrochloride, codeine phosphate, tranilast, dextromethorphan hydrobromide, dimemorfan phosphate, clobutinol hydrochloride, fominoben hydrochloride, benproperine phosphate, eprazinone hydrochloride, clofedanol hydrochloride, ephedrine hydrochloride, noscapine, pentoxyverine citrate, oxeladin citrate and isoaminyl citrate; (11) expectorants such as bromhexine hydrochloride, carbocisteine, ethyl cysteine hydrochloride and methylcysteine hydrochloride; (12) bronchodilators such as theophylline, aminophylline, sodium cromoglicate, procaterol hydrochloride, trimetoquinol hydrochloride, diprophilline, salbutamol sulfate, clorprenaline hydrochloride, formoterol fumarate, orciprenaline sulfate, pilbuterol hydrochloride, hexoprenaline sulfate, bitolterol mesilate, clenbuterol hydrochloride, terbutaline sulfate, malbuterol hydrochloride, fenoterol hydrobromide and methoxyphenamine hydrochloride; (13) cardiacs such as dopamine hydrochloride, dobutamine hydrochloride, docarpamine, denopamine, caffeine, digoxin, digitoxin and ubidecarenone; (14) diuretics such as furosemide, acetazolamide, triclormethiazide, methylclothiazide, hydrochlorothiazide, hydroflumethiazide, ethiazide, cyclopenthiazide, spironolactone, triamterene, florothiazide, pretanide, mefruside, etacrynic acid, azosemide and clofenamide; (15) muscle relaxants such as chlorphenesin carbamate, tolperisone hydrochloride, eperisone hydrochloride, tizanidine hydrochloride, mephenecine, chlorzoxazone, phenprobamate, methocarbamol, chlormezanone, pridinol mesilate, afloqualone, baclofen and dantrolene sodium; (16) cerebral metabolism ameliorants such as nicergoline, meclofenoxate hydrochloride and tartireline; (17) minor tranquilizers such as oxazolam, diazepam, clotiazepam, medazepam, temazepam, fludiazepam, meprobamate, nitrazepam and chlordiazepoxide;

(18) major tranquilizers such as sulpiride, clocapramine hydrochloride, zotepine, chlorpromazine and haloperidol; (19) β-blockers such as bisoprolol fumarate, pindolol, propranolol hydrochloride, carteolol hydrochloride, metoprolol tartrate, labetanol hydrochloride, acebutolol hydrochloride, bufetolol hydrochloride, alprenolol hydrochloride, arotinolol hydrochloride, oxprenolol hydrochloride, nadolol, bucumorol hydrochloride, indenolol hydrochloride, timolol maleate, befunolol hydrochloride and bupranolol hydrochloride; (20) antiarrthymics such as procainamide hydrochloride, disopyramide phosphate, cibenzoline succinate, ajmaline, quinidine sulfate, aprindine hydrochloride, propafenone hydrochloride, mexiletine hydrochloride and ajmilide hydrochloride; (21) athrifuges such as allopurinol, probenecid, colistin, sulfinpyrazone, benzbromarone and bucolome;

(22) anticoagulants such as ticlopidine hydrochloride, dicumarol, potassium warfarin, and (2R,3R)-3-acetoxy-5-[2-(dimethylamino)ethyl]-2,3-dihydro-8-methyl-2-(4-methylphenyl)-1,5-benzothiazepin-4(5H)-one maleate; (23) thrombolytics such as methyl(2E, 3Z)-3-benzylidene-4-(3,5-dimethoxy-α-methylbenzylidene)-N-(4-methylpiperazin-1-yl) succinamate hydrochloride; (24) liver disease drugs such as (±)r-5-hydroxymethyl-t-7-(3,4-dimethoxyphenyl)-4-oxo-4,5,6,7-tetrahydrobenzo[b] furan-c-6-carboxylactone; (25) antiepileptics such as phenytoin, sodium valproate, metalbital and carbamazepine;

(26) antihistamines such as chlorpheniramine maleate, clemastine fumarate, mequitazine, alimemazine tartrate, cyproheptadine hydrochloride and bepotastin besilate; (27) antiemitics such as difenidol hydrochloride, metoclopramide, domperidone and betahistine mesilate and trimebutine maleate; (28) depressors such as dimethylaminoethyl reserpilinate dihydrochloride, rescinnamine, methyldopa, prazocin hydrochloride, bunazosin hydrochloride, clonidine hydrochloride, budralazine, urapidil and N-[6-[2-[(5-bromo-2-pyrimidinyl)oxy]ethoxy]-5-(4-methylphenyl)-4-pyrimidinyl]-4-(2-hydroxy-1,1-dimethylethyl)benzene sulfonamide sodium; (29) hyperlipidemia agents such as pravastatin sodium and fluvastatin sodium;

(30) sympathetic nervous stimulants such as dihydroergotamine mesilate and isoproterenol hydrochloride, etilefrine hydrochloride; (31) oral diabetes therapeutic drugs such as glibenclamide, tolbutamide and glimidine sodium; (32) oral carcinostatics such as malimastat; (33) alkaloid narcotics such as morphine, codeine and cocaine; (34) vitamins such as vitamin B1, vitamin B2, vitamin B6, vitamin B12, vitamin C and folic acid; (35) thamuria therapeutic drugs such as flavoxate hydrochloride, oxybutynin hydrochloride and terolidine hydrochloride; and, (36) angiotensin converting enzyme inhibitors such as imidapril hydrochloride, enalapril maleate, alacepril and delapril hydrochloride.

Preferable examples include diltiazem hydrochloride, theophylline, acetaminophen, aspirin, ibuprofen, dextromethorphan hydrobromide and disopyramide phosphate.

A drug powder having a mean length of the long axis of 50 μm or less, and preferably 20–40 μm is used for the drug powder. The drug may be crushed to the desired particle size prior to granulation. Although crushing is performed with conventional methods such as crushing using a fine crusher, extremely fine particles (mean length of the long axis of 1 µm or less) are not preferred and should be avoided.

The amount of drug used is 97 wt % or less of the granulation product, preferably 40–90 wt %, and particularly preferably within the range of 50–70 wt % of the granulation product.

[3] The binder used in the method of the present invention refers to that which dissolves in a solvent and has the property of binding drug particles and solvent-retaining excipient particles, and the binder is suitably selected according to type, amount and so forth of solvent, drug and solvent-retaining excipient.

The binder preferably has solubility at 25° C. of 10 g or more, and particularly preferably 20 g or more, per 1 liter of solvent. In addition, in the case of a water-containing solvent, that having solubility at 25° C. of 10 g or more, and particularly 20 g or more, per 1 liter of water in the solvent can be used preferably.

Specific examples include hydroxypropyl cellulose, hydroxypropylmethyl celluloses (e.g., hydroxypropylmethyl cellulose, hydroxypropylmethyl cellulose phthalate and hydroxypropylmethyl cellulose acetate succinate), polyvinyl alcohol, dextrin, polyvinyl pyrrolidone, polyacrylic acid, polymethacrylic acid, gum arabic, gelatin and agar.

Preferable examples include hydroxypropylcellulose, hydroxypropylmethyl cellulose and polyvinylpyrrolidone, while hydroxypropyl cellulose is most preferable.

Although the amount of binder used varies according to the amounts of drug powder and solvent-retaining excipient powder, particle size, binding strength of the binder, viscosity of the solution of binder and so forth, it is normally used within the range of 0.1–10 wt %, and preferably 0.5–5 wt %, of the drug.

[4] The solvent used for the binder solvent used in the method of the present invention dissolves the binder while also having the property of being retained by the solvent-retaining excipient, and that which dissolves the drug but does not react with the drug is used preferably.

Such a solvent is suitably selected from those solvents that are normally used in the field of pharmaceutics according to the type and so forth of the drug, solvent-retaining excipient and binder.

Specific examples include water, alcohol solvents (e.g., lower alkanols that may or may not be substituted such as methanol, ethanol, n-propyl alcohol, isopropyl alcohol, 2-methoxyethanol, 2-ethoxyethanol), ketone solvents (e.g., lower alkyl ketones such as acetone and methyl ethyl ketone), ester solvents (e.g., lower alkyl esters of acetic acid such as ethyl acetate ester) and their mixed solvents. Preferable examples include water and aqueous solvents, while water and aqueous solvents (such as aqueous lower alkanols such as aqueous ethanol) are the most preferable.

Although the amount of solvent used varies according to the solubility of the drug and binder, solvent absorption rate of the solvent-retaining excipient and so forth, it is normally 0.1–3 ml, and preferably 0.3–1.5 ml, per 1 g of drug.

[5] Although other additives may be contained as necessary when producing the spherical fine particles as claimed in the present invention, in order to obtain particles having a high drug content, it is preferable if the amount of such additives is low. The amount of additives added can be suitably adjusted according to the type of drug, solvent-retaining excipient, binder and solvent.

Additives having high solubility in the solvent are effective in cases when the solubility of the drug in the solvent is low. In the case of using an aqueous solvent for the solvent, examples of conventionally used water-soluble additives include water-soluble sugars, and preferably lactose, sucrose, mannitol and sorbitol.

Additives for preventing particle aggregation are added in the case of aggregation occurring in the resulting particles. In the case of using a water-containing solvent for the solvent, examples of additives for preventing aggregation of the resulting particles include alkaline earth metal phosphates (calcium phosphate), alkaline earth metal silicates (synthetic calcium silicate), alkaline earth metal stearates (calcium stearate and magnesium stearate) and talc.

In addition, finely granulated talc, titanium oxide and other surface improvers may be used to smooth the surface of the resulting particles.

The following provides an explanation of the method of the present invention.

According to the present invention, the above-mentioned binder solution is added to a mixture containing the above solvent-retaining excipient powder and drug powder and other of the above additives are added as necessary followed by applying to a high-speed mixing granulation to produce spherical fine particles.

Examples of granulating machines that can be used for high-speed mixing granulation include agitating granulating machines having an agitator (e.g., rotor disk, agitator or agitating blade) [for example, Super Mixer (Kawada Seisakusho), Henschel Mixer (Mitsui-Miike Seisakusho), GRAL (Fuji Paudal Co., Ltd.), Vertical Granulator (Fuji Sangyo), Pharmamatrix (Nara Kikai Seisakusho), High-Speed Mixer (Fukae Kogyo), Agromaster (Hosokawa Micron) and New-gramachine (Seishin Enterprise)]. In addition, the agitating granulating machine may have a crusher having a rotating shaft perpendicular to the rotating shaft of the agitator (e.g., chopper, cross screw or lamp breaker). Of these, an agitating granulating machine having an agitating blade, such as the Agromaster or New-gramachine, can be used particularly preferably.

The rotating speed of the agitator in the agitating granulating machine is such that the rotational linear velocity of the resulting particles is preferably 200–2000 m/min, and particularly preferably 300–1000 m/min.

Although it is not particularly necessary to regulate the granulation temperature (outside temperature), granulation may be performed while cooling as necessary in consideration of drug stability.

Solvent-retaining excipient and other solid components may be loaded into the granulating machine without mixing or after mixing.

Loading of binder solution during granulation may be performed after loading drug, vehicle-retaining excipient and other solid components, by loading all at once, loading separately, or loading at a fixed speed. The binder solution is suitably selected according to the type of drug, solvent-retaining excipient, etc., solvent, viscosity of binder solution and so forth. Loading may also be performed by spraying or dropping as necessary.

Granulation time is suitably selected according to the type of solvent-retaining excipient, etc., type and amount of solvent, viscosity of the binder solution and so forth. In general, the end point of granulation can be determined by monitoring the granulation process by measuring power consumption (see Pharmacology Journal 107(5), pp. 377–383 (1987)). Granulation time is normally about 0.1–5 hours, and preferably about 0.4–3 hours.

Drying temperature of the particles is suitably selected according to drug stability and type of solvent. Drying temperature is normally 70° C. or less, and preferably 0–50° C. Pressure may also be reduced as necessary. Drying time can be shortened by raising the temperature and/or lowering the pressure. Drying time is normally 1–24 hours, and preferably 3–16 hours. Conventionally used methods such as fluidized drying, shelf drying and so forth are employed for the drying method.

According to the method of the present invention, spherical fine particles having a mean particle size of 200 μm or less can be produced at a yield of 90 wt % or more of the solid components used for granulation. In addition, depending on the conditions, spherical fine particles having a mean particle size of 200 μm or less can be produced at a yield of 95% or more of the solid components. In general, as production scale increases and the granulating machine becomes larger, yield improves since raw materials fleeing from outside the granulating machine in the granulation process decrease.

The mean particle size of the spherical fine particles formed is 200 μm, and normally 60–200 μm. The preferable particle size of the spherical fine particles is 60–150 μm.

The particle size distribution of said particles is such that particles measuring 40 μm or less account for 10 wt % or less, and particles measuring 200 μm or more account for 10 wt % or less. The preferable article size distribution is such that particles measuring 60 μm or less account for 20 wt % or less, and particles measuring 150 μm or more account for 20% wt % or less. In addition, said particles have high sphericity, and the mean aspect ratio (long axis/short axis) is 1–1.5, and preferably 1–1.2.

Although the surfaces of the spherical particles formed are generally smooth, in general, the particles tend to become smoother in the case of high solubility of the drug in the solvent.

In this manner, since the spherical fine particles produced with the method of the present invention that contain drug and have a mean particle size of 200 μm or less not only have a small mean particle size, but also have a narrow size distribution width (little variation in particle size), small mean aspect ratio (high sphericity) and smooth surfaces, it is easy to coat the surfaces of these spherical fine particles.

Coated spherical fine particles can be produced from the drug-containing spherical fine particles produced in the manner described above by coating with a fine particle coating method known in the prior art.

Examples of such coating methods include protecting coating, gastrosoluble coating, enteric coating and slow-release coating.

With respect to these coating methods and the raw materials used for coating, the methods or materials described on pages 515–527 of the Granulation Handbook (Japan Powder Industry Technology Association ed., Ohm Publishing) can be used by suitably selecting according to the specific objective. In addition, coated spherical fine particles can be produced by making suitable alterations in consideration of the properties of the drug and so forth contained in the drug-containing spherical fine particles based on the descriptions of the Chem. Pharm. Bull. 35, 2949 (1987), Chem. Pharm. Bull. 36, 1491 (1988), Chem. Pharm. Bull. 36, 3070 (1988), Chem. Pharm. Bull. 36, 4927 (1988), Pharm. Tech Japan Vol. 9, No. 7, 55 (811) (1993) and so forth.

Specific technologies of coating methods are as listed below, and the drug-containing spherical particles as claimed in the present invention are coated in accordance with these methods.

Examples of specific technologies include Japanese Unexamined Patent Publication No. 4-235123 (coating with a water-insoluble and water-impermeable acrylic resin polymer containing alkaline earth metal stearate-trimethyl ammonium ethyl group), Japanese Unexamined Patent Publication No. 2-1405 (coating with a porous film comprised of hydrophobic polymer substance or hydrophobic polymer substance and hydrophilic polymer substance and having porosity of about 0.4–0.9), Japanese Patent Application No. 10-211677 (coating with a multilayer film containing an hydrophobic organic compound-water-soluble polymer mixture in which adjacent layers are mutually different), Japanese Unexamined Patent Publication No. 2-121918 (coating with a coating that controls the release of a drug not sensitive to pH changes, and a coating composed of alternating hydrophilic and hydrophobic layers), Japanese Unexamined Patent Publication No. 8-26977 (coating with a mixture of enteric coating agent and water-insoluble coating agent), Japanese Patent Application No. 10-211678 (coating with a mixture of hydrophobic organic compound and enteric polymer), and a patent application dated the same as the present application (spray coating with an ethanol solution of stearic acid and ethyl cellulose).

The coated drug-containing spherical fine particles can be formulated into easily-swallowed, controlled-release preparations using these methods.

Examples of easily-swallowed, controlled release preparations include orally rapid-disintegrating preparations, suspensions and powders (fine particles).

For example, an orally rapid-disintegrating preparation is produced according to the known methods listed below.

Examples of such methods include Japanese Patent Application No. 9-107991 (molding drug formulation components consisting of a drug and preparation additives at low density, followed by wetting with alcohol, and followed by removal of that alcohol), Japanese Unexamined Patent Publication No. 5-271054 (tablet formation of a mixture containing drug, sugar and moisture), Japanese Unexamined Patent Publication No. 8-291051 (tablet formation of a mixture of drug, water-soluble binder and water-soluble excipient followed by humidifying with water vapor and drying), WO 93/15724 (compression of a mixture containing only water-soluble additive, drug and water, and glazing after drying), WO 93/12769 (suspending a drug and sugar in agar aqueous solution and solidifying into a jelly followed by drying), and WO 95/20380 (granulation of a drug and a sugar having low moldability with a sugar having high moldability followed by compression of the granulation product).

In addition, examples of suspensions include syrups (including dry syrups) described in A-110 through A-115 of the Explanation of the 12th edition of the Japanese Pharmacopeia, and are produced in accordance with that description.

Furthermore, coated drug-containing spherical microparticles can also be used in the production of conventionally used preparations such as capsules and tablets.

BEST MODE FOR CARRYING OUT THE INVENTION

Figure 1:
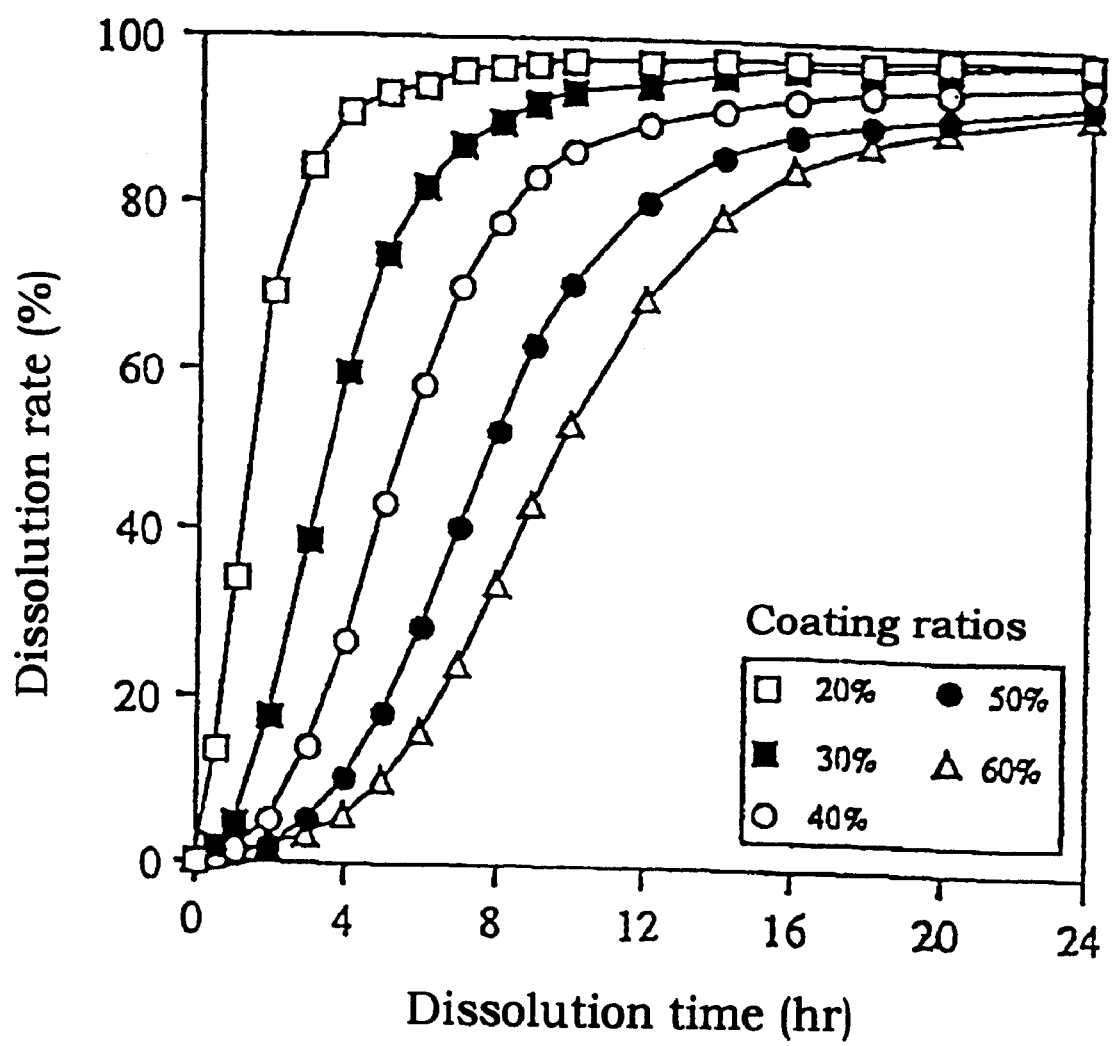
FIG. 1 shows the results of an elution test of a drug in the case of changing the coating ratio.

The following provides a detailed explanation of the present invention through its examples. However, it should be interpreted that the present invention is not limited by these examples.

EXAMPLE 1

80 Parts of diltiazem hydrochloride crushed with a hammer mill (Fuji Paudal Co., Ltd.) (mean particle size: approx.

25 μm) and 19 parts of microcrystalline cellulose (mean particle size: approx. 25μm, trade name: Avicel PH-M25 (Asahi Chemical Industry)) were charged into the New-gramachine NC-200 (Seishin Enterprise) having a diameter of the centrifugal granulator of 20 cm and mixed well. While continuing to stir this at 30° C. and 700 rpm, a solution was added containing 1 part of hydroxypropyl cellulose (trade name: HPC-SL (Nippon Soda)) dissolved in a mixed liquid of 79 parts ethanol and 20 parts water followed by granulation for 25 minutes. Following granulation, the particles were dried on a drying shelf for 3 hours at 45° C. to obtain spherical fine particles.

Yield [fine particles/(diltiazem hydrochloride+microcrystalline cellulose+hydroxypropyl cellulose)×100]: 95%.

EXAMPLE 2

60 Parts of theophylline crushed with a hammer mill (Fuji Paudal Co., Ltd.) (mean particle size: approx. 30 μm), 24 parts of mannitol and 14 parts of microcrystalline cellulose (mean particle size: approx. 25 μm, trade name: Avicel PH-M25 (Asahi Chemical Industry)) were charged into the New-gramachine NC-200 (Seishin Enterprise) having a diameter of the centrifugal granulator of 20 cm and mixed well. While continuing to stir this at 35° C. and 550 rpm, a solution was added containing 2 parts of hydroxypropyl cellulose (trade name: HPC-SL (Nippon Soda)) dissolved in a mixed liquid of 68 parts ethanol and 30 parts water followed by granulation for 54 minutes. Following granulation, the particles were dried on a drying shelf for 3 hours at 45° C. to obtain spherical fine particles.

Yield [fine particles/(theophylline+microcrystalline cellulose+mannitol+hydroxypropyl cellulose)×100]: 97%.

EXAMPLE 3

90 Parts of diltiazem hydrochloride crushed with a hammer mill (Fuji Paudal Co., Ltd.) (mean particle size: approx. 25 μm) and 18 parts of cornstarch (mean particle size: approx. 10 μm) were charged into the Agromaster LABO2 (Hosokawa Micron) having a diameter of the centrifugal granulator of 20 cm and mixed well. While continuing to stir this at 23 ° C. and 350 rpm, a solution was added containing 2 parts of hydroxypropyl cellulose (trade name: HPC-SL (Nippon Soda)) dissolved in a mixed liquid of 78 parts ethanol and 20 parts water followed by granulation for 28 minutes. Following granulation, the particles were dried on a drying shelf for 3 hours at 45° C. to obtain spherical fine particles.

Yield [fine particles/(diltiazem hydrochloride+cornstarch+hydroxypropyl cellulose)×100]: 97%

The particle size distribution and mean particle size were measured for each fine particle preparation produced in Examples 1 through 3 above using a sieve shaker, and those results are shown in Tables 1 and 2.

TABLE 1

|  | 40 μm or less | 40–200 μm or less | 200 μm or more |
| --- | --- | --- | --- |
| Example 1 | 1.7% (w/w) | 97.2% | 1.1% |
| Example 2 | 3.4% | 94.8% | 1.8% |
| Example 3 | 6.8% | 87.6% | 5.6% |

Measurement of particle size distribution in Table 1 was performed by sampling 10 g of granulation product, shaking for 3 minutes using sieves having a mesh size of 40 μm and 200 μm, respectively measuring the weights of the screened granulation products, and calculating wt %.

As is clear from the results of measuring particle size distribution, fine particles produced in accordance with the method of the present invention have a mean particle size of about 100 μm, and 85% of those particles fall within the range of a particle size of 40–200 μm. In addition, the shapes of the granulation products as observed with a scanning electron microscope were all spherical.

TABLE 2

| Example 1 | 79 μm |
| --- | --- |
| Example 2 | 119 μm |
| Example 3 | 108 μm |

Measurement of mean particle size in Table 2 was performed by stacking up sieves having different mesh sizes (mesh sizes: 350, 250, 177, 149, 125, 105, 74, 40 and 0 μm), adding 10 g of sampled granulation product and shaking for 3 minutes followed by measuring the weights of the granulation products remaining on each sieve. The granulation product remaining on each sieve was assumed to have a diameter of an intermediate value between the mesh size of that sieve and the mesh size of the sieve immediately above it, and a weighted average was obtained by multiplying this by weight.

EXAMPLE 4

The drug-containing spherical fine particles obtained in Example 1 were shaken using a sieve having a mesh size of 150 μm to acquire only those drug-containing spherical fine particles that passed through the sieve. Yield: 96.6%

EXAMPLE 5

A solution comprising stearic acid (Kao) (2.5%), ethyl cellulose #10 (Nisshin Kasei) (2.5%) and ethanol (95%) was spray coated onto 100 g of the drug-containing spherical fine particles obtained in Example 4 using a Wurster fluidized bed coating apparatus (Model GPCC-1, Glatt) followed by drying until the temperature of the coated products reached 40° C. to produce coated fine particles.

According to this method, coated particles were obtained having coating ratios [(coated fine particle weight—drug-containing spherical fine particles)/weight of coated fine particles×100] of 20%, 30%, 40%, 50% and 60%.

EXPERIMENT EXAMPLE 1

Dissolution tests as described in the 13th edition of the Japanese Pharmacopeia (JP) were performed on the coated fine particles having the respective coating ratios obtained in Example 5 [test fluid: JP 2nd fluid (pH 6.8) 900 ml, temperature: 37° C., paddle rotating speed: 100 rpm], followed by measurement over time of the amount of diltiazem hydrochloride that eluted into the test liquid by high-performance liquid chromatography, after which dissolution rate (amount of diltiazem hydrochloride contained in the drug-containing spherical fine particles: 100%) was calculated from those results. Those results are shown in FIG. 1.

INDUSTRIAL APPLICABILITY

According to the method of the present invention, spherical fine particles having a high drug content and a mean particle size of 200 μm or less can be produced at high yield with a simple procedure.

In addition, since the drug-containing spherical fine particles obtained with the method of the present invention have high sphericity and smooth surfaces, and have a narrow particle size distribution, there is no impairment of coating uniformity when coated with various coatings and it is not necessary to use excessive coating agent, thereby enabling coating time to be reduced.

Moreover, use of the drug-containing spherical fine particles obtained with the method of the present invention allows the production of controlled-release preparations which, in addition to being easily-swallowed, have a pleasant sensation in the oral cavity when taken.

What is claimed is:

1. A preparation method of drug-containing spherical fine particles having a mean particle size of 60–200 μm comprising:

adding a binder solution to a mixture containing an excipient powder having the property of retaining a solvent and a drug powder, and rotary-granulating by high-speed wet-mixing for 0.1 to 5 hours at a rotational linear velocity of said agitating blade of 200 to 2000 m/min.

2. The preparation method of spherical fine particles according to claim 1, wherein spherical fine particles are produced at a yield of 90–100 wt % of solid component used for granulation.

3. The preparation method of spherical fine particles according to claim 1, wherein the drug content of said spherical fine particles is 40 to 90 wt %.

4. The preparation method of spherical fine particles according to claim 1, wherein the mean length of the long axis of the excipient powder having the property of retaining solvent is 1–40 μm, and the mean length of the long axis of the drug powder is 20–50 μm.

5. The preparation method of spherical fine particles according to claim 1, wherein the mean length of the long axis of the excipient powder having the property of retaining solvent is 1 to 30 μm, the mean length of the long axis of the drug powder is 20 to 40 μm, and the mean particle size of the spherical fine particles is 60 to 150 μm.

6. The preparation method of spherical fine particles according to any one of claims 1, 2, 3, 4 and 5, wherein the mean aspect ratio (long axis/short axis) of the spherical fine particles is 1 to 1.5.

7. The preparation method of spherical fine particles according to claim 1, wherein spherical fine particles having a particle size of 0–40 μm are 0–10 wt %, and spherical fine particles having a particle size of 200 μm or more are 0–10 wt %.

8. The preparation method of spherical fine particles according to claim 1, wherein the excipient having the property of retaining solvent is a water-retentive excipient, and the binder solution is a water-containing binder solution.

9. The preparation method of spherical fine particles according to claim 8, wherein the water retentivity of the water-retentive excipient is 5 to 30 wt %.

10. The preparation method of spherical fine particles according to claim 8 or 9, wherein the solubility of drug in water at 25° C. is at least 1 g/liter.

11. The preparation method of spherical fine particles according to claim 8, wherein the water-retentive excipient is selected from the group consisting of celluloses and starches, the binder is selected from the group consisting of hydroxypropyl cellulose, hydroxypropylmethyl cellulose, polyvinylpyrrolidone, dextrin, polyvinyl alcohol, polyacrylic acid, polymethacrylic acid, gum arabic, gelatin and agar, and the binder solution is selected from the group consisting of an aqueous solution of binder and a water-containing ethanol solution of binder.

12. A method of making coated spherical fine particles comprising:

producing drug-containing spherical fine particles with the method of claim 1, 2, 3, 4, 5, 7, 8 or 11; and coating the drug-containing spherical fine particles.

13. A method of making an orally rapidly-disintegrating tablet, suspension or powder, said method comprising:

using the coated spherical fine particles produced with the method according to claim 12.

14. Drug-containing spherical fine particles having a mean particle size of 60 to 200 μm producible with the method of claim 1, 2, 3, 4, 5, 7, 8 or 11.

15. A preparation method of drug-containing spherical fine particles having a mean particle size of 40–200 μm comprising:

adding a binder solution to a mixture containing an excipient powder having the property of retaining a solvent and a drug powder, and rotary-granulating by high-speed wet-mixing for 0.1 to 5 hours at a rotational linear velocity of said agitating blade of 200 to 2000 m/min.

16. The preparation method of spherical fine particles according to claim 15, wherein spherical fine particles are produced at a yield of 87.6 to 97.2 wt % of solid component used for granulation.

* * * * *